United States Patent [19]
Wikholm

[11] Patent Number: 6,096,326
[45] Date of Patent: *Aug. 1, 2000

[54] SKIN CARE COMPOSITIONS AND USE

[75] Inventor: Hugo Allan Wikholm, deceased, late of Ludvika, Sweden, by Torbjorn Claesson, Administrator of the Estate

[73] Assignee: Scandinavian-American Import/Export Corporation, Glendora, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/912,070

[22] Filed: Aug. 15, 1997

[51] Int. Cl.$^7$ ............................. A61K 7/021; A61K 7/06; A61K 7/00; A61K 6/00
[52] U.S. Cl. ......................... 424/401; 424/63; 424/70.1; 424/70.11; 514/887
[58] Field of Search ........................... 424/401, 63, 70.1, 424/70.11; 514/887

[56] References Cited

U.S. PATENT DOCUMENTS 5,539,129   7/1996   Zysman .................................. 549/430

OTHER PUBLICATIONS

Haruo, et al. Japanese Publication No. 58177908 A, published Oct. 18, 1983, "Cosmetic", *Patent Abstracts of Japan*.
Macfarlane, et al. (1981) Macadamia nuts as an edible oil source. *AOCS Monogr.* 9 (New Sources Fats Oils): 103–108.
Klein (1991) Kukui and macadamia nut oils: cosmetic applications, *Cosmet. Toiletries* 106(11): 87–88, 90.
International Cosmetic Ingredient Dictionary and Handbook, 7th Edition (1997) Edited by Wenninger, et al. 1:366, 765.
International Cosmetic Ingredient Dictionary and Handbook, 7th Edition (1997) Edited by Wenninger, et al. 3:2108, 2385.
Ako, et al. (1995) Healthful new oil from macadamia nuts. *Nutrition* 11(3);286–288.
Saleeb, et al. (1973) The oil and protein in nuts of *Macadamia tetraphylla* L. Johnson, *Macadamia integrifola* Maiden and Betche, and Their $F_1$ Hybrid. *J. Amer. Soc. Hort. Sci.* 98(5):453–456.

*Primary Examiner*—John Kight
*Assistant Examiner*—D. Faulkner
*Attorney, Agent, or Firm*—Foley & Lardner

[57] ABSTRACT

The invention provides compositions containing dermaphile oils and methods for their use. Preferred composition contain Purcellin Oil and are useful in treating a wide variety of adverse skin conditions, including disorders manifesting inflammatory and non-inflammatory symptoms and having a variety of etiologies. The compositions are especially useful in treating psoriasis, eczema, acne, surgical scars and sunburn, but are also useful in treating cuts, insect bites, pruritis, cold sores and dry skin. Methods for the use of these compositions are also provided.

18 Claims, No Drawings

SKIN CARE COMPOSITIONS AND USE

BACKGROUND OF THE INVENTION

Skin disorders affect millions of people annually in the United States alone. On a worldwide scale this figure is staggering. Such disorder range from the relatively minor inconvenience of dry skin to more serious life-threatening conditions.

One such condition is psoriasis, which alone affects approximately 8 million Americans. Psoriasis is a chronic proliferative skin disorder of unknown etiology. Symptoms include thickening of both dermal and epidermal layers, with cellular proliferation and inflammation. The symptoms or psoriasis range from relatively mild irritation to death. Currently treatment of psoriasis is generally topical, using emollients, keratolytics and corticosteroids. In severe cases, however, systemic corticosteroids and antimetabolites, such as methotrexate, are used. In view, however of the unknown etiology of the disease, rationale design of effective therapeutics for use in treatment regimes has been unavailing. Accordingly, there exists an unmet need for effective compositions for the treatment of psoriasis.

Another such disorder is eczema. Eczema, sometimes known as dermatitis, results from an inflammatory response to either endogenous or exogenous agents. The disorder is characterized by erythema, vesicles, scales and itching. More advanced symptoms include edema, serous discharge and crusting. In chronic eczema, the skin becomes thickened, leathery and hyperpigmented. Although medicaments exist for the treatment of eczema, none is completely satisfactory or universally accepted. Thus, there is an ongoing need for additional effective agents for treating this disease.

Further examples of skin disorders for which adequate treatment is unavailable or insufficient include acne, cold sores, dry skin, sunburn, cuts, insect bites, pruritic lesions and other inflammatory and non-inflammatory lesions of the skin. Accordingly, there is a need for a safe and effective agent, suitable for topical delivery, that is useful in treating this wide variety of skin conditions.

SUMMARY OF THE INVENTION

It is therefore an object of the present invention to provide compositions suitable for topical delivery that are useful in treating adverse skin conditions.

According to this object of the invention, compositions comprising a dermaphile oil, which are suitable for topical treatment of adverse skin conditions, are provided. According to this same object compositions comprising Purcellin Oil are provided. Further according to this object, compositions are provided which comprise Purcellin Oil in combination with other cosmetic and pharmaceutical agents.

It is another object of the invention to provide methods of using the therapeutic and pharmaceutical compositions of the invention to treat adverse skin conditions.

According to this object of the invention, methods are provided for treating adverse skin conditions using compositions comprising Purcellin Oil.

DETAILED DESCRIPTION OF THE PREFERRED EMBODIMENTS

The present invention is based on the observation that dermaphile oils, such as Purcellin Oil (also known as cetearyl octanoate) are useful in treating a wide variety of adverse skin conditions, including disorders manifesting inflammatory and non-inflammatory symptoms and having a variety of etiologies. The compositions are useful in treating, for example, psoriasis, eczema, acne, cold sores, dry skin, sunburn, cuts, insect bites, scarring, lesions caused by infectious agents or parasites and pruritis.

Compositions of the Invention

The compositions of the invention typically comprise a dermaphile oil, preferably Purcellin Oil, as an active ingredient. A dermaphile oil is any oil, suitable for cosmetic or pharmaceutical topical applications, which does not prevent the skin from breathing. Preferred compositions comprise Purcellin Oil in an amount from 0.5% to 5% w/w, not accounting for any optional propellant. Preferred compositions contain Purcellin Oil in a topical formulation.

Purcellin Oil is variously marketed under the alternate names: cetearyl octanoate; cetyl/stearyl 2-ethylhexanoate; crodamol CAP; 2-ethylhexanoic acid, cetyl/stearyl ester; and schercemol 1688. As demonstrated in Example 9, below, analysis of a typical sample reveals three primary ingredients, isopropyl myristate, C16 (cetyl) ethylhexanoate and C18 (stearyl) ethylhexanoate.

Topical formulations include cosmetic and pharmaceutical formulations. Specifically, these include formulations for transdermal delivery, ointments, creams, pastes, lotions, topical solutions, topical tinctures, liniments, collodions glycergelatins, plasters, powders, aerosol sprays, non-aerosol sprays, gels, sunscreens and shampoos.

Topical formulations typically comprise topically acceptable vehicles. A topically acceptable vehicle is one that does not cause skin irritation, yet is compatible with dermaphile oils. Examples of these vehicles can be found in PHARMACEUTICAL DOSAGE FORMS AND DRUG DELIVERY SYSTEMS, 5th ed. (Lea & Febiger 1990), at pages 322–345, and in Chapters 83 and 87 of REMINGTON'S PHARMACEUTICAL SCIENCES, 18th ed. (Mack Publishing Co. 1990) which are hereby incorporated by reference. Such vehicles can be aqueous or non-aqueous. Examples of these vehicles include hydrocarbon bases, emulsion bases and water-soluble bases.

A preferred topically acceptable vehicle contains Eutanol G (octyldecanol) and an alcohol, such as ethanol. Preferred ethanols include denatured ethanols, such as SD alcohols, and specifically include SD Alcohol 39 C. The amount of each ingredient is usually calculated disregarding any contribution by the optional propellant. Some preferred compositions contain from about 40% to about 80% w/w Eutanol G, while other preferred compositions contain from about 45% to about 60% Eutanol G. Most preferred compositions contain from about 48% to about 55% Eutanol G. Preferred compositions also typically contain from about 20% to about 50% w/w ethanol, while other preferred compositions contain from about 40% to about 50% w/w of a denatured ethanol. Most preferred compositions contain from about 46% to about 49% SD Alcohol 39 C.

Aerosol compositions typically include at least one hydrocarbon-based propellant, such as propane or butane. Preferred aerosol compositions contain both propane and butane in an amount from about 20% to about 30% w/w, taking into account all ingredients. Other preferred compositions contain propane or butane in an amount from about 20% to about 30% w/w, taking into account all ingredients. Most preferred aerosol compositions contain a hydrocarbon propellant in an amount from about 23% to about 28% w/w, taking into account all ingredients.

The compositions of the invention may also contain other cosmetic and pharmaceutical agents known in the art for treating adverse skin conditions or cosmetic skin conditions.

Cosmetic and pharmaceutical agents my include any chemical substances natural or synthetic, intended for topical application to the skin or its appendages in human and animals. Some examples of cosmetic and pharmaceutical agents include ages spots and keratoses removing agents, analgesics, anesthetics, antiacne agents antibacterial agents, antiyeast agents, antifungal agents, antiviral agents, antiburn agents, antidandruff agents, antidermatitis agents, antipruritic agents antiperspirants antiinflammatory agents, antihyperkeratolytic agents, andidryskin agents, antipsoriatic agents, antiseborrheic agents, astringents, softeners, emollient agents, coal tar, bath oils, sulfur, rinse conditioners, foot care agents, hair growth agents, powder, shampoos, skin bleaches, skin protectants, soaps, cleansers, antiaging agents, sunscreen agents, wart removers, wet dressings, vitamins, tanning agents, topical antihistamine agents, hormones, vasodilators, retinoids, and other dermatologicals. These cosmetic and pharmaceutical agents typically would be present in the inventive composition in a therapeutically or cosmetically effective amount, as determined as appropriate by the clinician, or other health care or cosmetic care professional.

Preparation of the Compositions of the Invention

To prepare a composition containing a dermaphile oil, the oil is typically dissolved in a solution which may contain ethanol, water, propylene glycol, acetone or other topically acceptable vehicles discussed above. The concentration of the dermaphile oil may range from about 0.1% to about 10% w/w, not including contribution of the optional propellant, however concentrations in the range of about 0.5% to 5% are preferred. Most preferred compositions contain 0.5%–1.5% dermaphile oil.

In preparing the inventive compositions as a cream or an ointment, the dermaphile oil is dissolved in a solvent such as water, ethanol, acetone, propylene glycol or polysorbate 80. The solution is then mixed with a conventional cream or ointment base, such as hydrophilic ointment or petrolatum. The concentration of the dermaphile oil may range from about 0.1% to about 10% w/w, not including contribution of the optional propellant, however concentrations in the range of about 0.5% to 5% are preferred. Most preferred compositions contain 0.5% to 1.5% dermaphile oil.

The present compositions may also be prepared as a gel, shampoo, spray, or stick. In a typical gel composition, a dermaphile oil is mixed into a suitable solvent. A suitable gelling agent is then added to the mixture. Suitable gelling agents in include hydroxyethylcellulose, hydroxypropylcellulose, hydroxypropylmethylcellulose, and ammoniated glycerrhizinate. The gelling agent is preferably present in the range of 0.1 to 4 percent by weight. The concentration of the dermaphile oil may range from about 0.1% to about 10% w/w, however concentrations in the range of about 0.5% to 5% are preferred. Most preferred compositions contain 0.5% to 1.5% dermaphile oil. When spray compositions are formulated, final concentrations are calculated disregarding the contribution of any propellant.

Methods of the Invention

The methods of the invention typically comprise administering to a subject, suffering from an adverse skin condition, a composition as described above. Although the subject is preferably human, the invention also contemplates veterinary applications of similar scope.

Adverse skin conditions include disorders manifesting inflammatory and non-inflammatory symptoms and having a variety of etiologies. Specific examples include psoriasis, eczema, acne, cold sores, dry skin, sunburn, cuts, insect bites, pruritis, dermatitis, keratosis, wrinkled skin, chapping, scarring, surgical scarring, cracking, and lesions caused by infectious agents or parasites. Lesions can be caused by infectious agents including bacteria, fungi and viruses, especially herpesviruses. Thus, nearly any lesion of the skin, regardless of etiology may be treated according to the invention.

Administering the inventive compositions may be accomplished using any means compatible with topical use. These include, for example, transdermal patches, direct manual application and spraying. Spraying can be accomplished, for example, using aerosol or pump-type mechanisms. The inventive compositions can be administered topically to any external surface of the body, including skin, hair and nails.

Although the amount and frequency of administration will vary with both the nature of the condition being treated and the concentration of the active ingredient, preferred methods utilize compositions containing 0.5% to 1.5% Purcellin Oil, which is applied from 1 to 6 times daily, as needed. Most preferred methods comprise applying a thin film of an inventive composition three times daily. Once symptoms have mitigated, maintenance treatment may be accomplished by once weekly applications.

The term "treating" in its various grammatical forms in relation to the present invention refers to preventing, curing, reversing, attenuating, alleviating, minimizing, suppressing or halting the deleterious effects of a disease state, disease progression, disease causative agent (e.g., bacteria, viruses or parasite), cosmetically undesireable or other abnormal condition.

The following examples are presented merely for illustrative purposes and are not meant to be limiting. All percentages are w/w, relative to the total weight of specified ingredients.

EXAMPLE 1

This example provides a typical topical formulation, suitable for use in the inventive methods. Purcellin Oil 0.5 gram is thoroughly mixed with Eutanol 69.5 grams and ethanol 30 grams. The resulting composition contains 0.5% Purcellin Oil, 69.5% Eutanol and 30% ethanol.

EXAMPLE 2

This example provides a typical topical formulation, suitable for use in the inventive methods. Purcellin Oil 0.930 gram is thoroughly mixed with Eutanol 48.639 grams and SD Alcohol 39 C 43.431 grams. The resulting composition contains 1% Purcellin Oil, 52.3% Eutanol and 46.7% SD Alcohol 39 C.

EXAMPLE 3

This example provides a typical aerosol formulation, suitable for use in the inventive methods. Purcellin Oil 0.930 gram is thoroughly mixed with Eutanol 48.639 grams and SD Alcohol 39 C 43.431 grams and added to 15 grams of butane propellant and 15 grams of propane propellant. The resulting composition contains 0.75% Purcellin Oil, 39.54% Eutanol and 35.31% SD Alcohol 39 C, 12.20% butane and 12.20% propane, accounting for all ingredients on a w/w basis. The relative proportions of the ingredients, other than the propellant, in the aerosol composition are the same as the non-aerosol formulations, such as that of Example 2.

EXAMPLE 4

This example provides a typical aerosol formulation, suitable for use in the inventive methods. Purcellin Oil 0.930 gram is thoroughly mixed with Eutanol 48.639 grams and SD Alcohol 39 C 43.431 grams and added to 30 grams of butane propellant. The resulting composition contains 0.75% Purcellin Oil, 39.54% Eutanol and 35.31% SD Alcohol 39 C, 24.39% butane, accounting for all ingredients on a w/w basis. The relative proportions of the ingredients, other than the propellant, in the aerosol composition are the same as the non-aerosol formulations, such as that of Example 2.

EXAMPLE 5

This example provides a typical aerosol formulation, suitable for use in the inventive methods. Purcellin Oil 0.930 gram is thoroughly mixed with Eutanol 48.639 grams and SD Alcohol 39 C 43.431 grams and added to 30 grams of propane propellant. The resulting composition contains 0.75% Purcellin Oil, 39.54% Eutanol and 35.31% SD Alcohol 39 C, 24.39% propane, accounting for all ingredients on a w/w basis. The relative proportions of the ingredients, other than the propellant, in the aerosol composition are the same as the non-aerosol formulations, such as that of Example 2.

EXAMPLE 6

This example provides a therapeutic composition according to the invention for use in treating eczema, psoriasis and other inflammatory and pruritic skin conditions. It uses a combination of Purcellin Oil and triamcinolone acetonide as active ingredients. Triamcinolone acetonide 0.1 gram and Purcellin Oil 1.5 grams are dissolved in 10 ml of ethanol. The resulting solution is mixed with 88 grams of ointment USP. The composition thus formulated contains approximately 0.1% triamcinolone acetonide and 1.5% Purcellin Oil.

EXAMPLE 7

This example provides a therapeutic composition according to the invention for use in treating inflammatory and/or pruritic skin conditions. It uses a combination of Purcellin Oil and hydrocortisone as active ingredients. Hydrocortisone 0.5 grams and Purcellin Oil 1 gram are dissolved in 10 ml of ethanol and 4 ml of acetone. The resulting solution is mixed with 84 grams of ointment USP. The composition thus formulated contains approximately 0.5% hydrocortisone and 1% Purcellin Oil.

EXAMPLE 8

This example provides a therapeutic composition according to the invention for use in treating eczema, psoriasis and other inflammatory and pruritic skin conditions. It uses a combination of Purcellin Oil and clobetasol propionate as active ingredients. Clobetasol propionate cream 99 grams and Purcellin Oil 1.5 grams are thoroughly mixed. The composition thus formulated contains approximately 0.05% clobestasol propionate and 1.5% Purcellin Oil.

EXAMPLE 9

This example provides a sunscreen composition containing octyl dimethyl PABA, dioxybenzonone and Purcellin Oil. Octyl dimethyl PABA 5 grams, dioxybenzonone 3 grams and Purcellin Oil 1 gram are dissolved in a mixture of ethanol 65 ml and propylene glycol 15 ml with stirring until homogenous. The composition thus formulated contains 5% octyl dimethyl PABA, 3% dioxybenzonone and 1% Purcellin Oil.

EXAMPLE 10

This example demonstrates the use of a preferred composition, as disclosed in Example 3, in treating adverse skin conditions. All subjects were followed for eight weeks, twice weekly.

Three subjects were included in the study:

One subject, a 36 year old white male suffering for ten years from what had been diagnosed as neuro-dermatitis by several physicians. Applications of the inventive composition, according to the methods disclosed herein, reduced itching and promoted considerable skin healing. There were significant changes in the condition of the skin when compared to onset and other treatments.

Another subject, a 65 year old white female had suffered for three years from what was diagnosed as postsurgical psoriasis. Applications of the inventive composition reduced itching, redness, scaling and pain by 50% and continued applications reduced the number of acute episodes.

A third subject was a 34 year old white female with an ongoing history of sensitivity to soaps, manifesting in split fingertips. Daily topical application resulted in clearing of chronic splitting of the skin. Decreased sensitivity to soap was observed when the inventive composition was applied before hand immersion in water and/or contact with soaps.

Two of the subjects had problems including itching episodes that were reduced considerably as a result of treatment. All three of the subjects showed healing of tissue. Scaling was reduced in two of the subjects. Two subjects showed reduced inflammation.

EXAMPLE 11

This example provides a typical composition of Purcellin Oil. A liquid sample was analyzed using standard gas chromatographic methods. The approximate concentrations for the major components were found to be as follows:

| Component | Concentration (%, w/w) |
| --- | --- |
| Isopropyl myristate | 8.5 |
| C14 (myristyl) ethylhexanoate | 0.6 |
| C16 (cetyl) ethylhexanoate | 50 |
| C17 ethylhexanoate | 0.2 |
| C18 (stearyl) ethylhexanoate | 27 |
| C20 (arachidyl) ethylhexanoate | 0.15 |

EXAMPLE 12

The subject was diagnosed with psoriasis by a dermatologist and presented with widespread scaling, edema and inflammation on the arms, stomach and back. The patient was provided with a composition according to Example 3 and conducted a topical self-treatment regimen according to the inventive methods. Progress was monitored using photographs. Treatment resulted in nearly complete elimination of scaling and marked decrease in inflammation and edema on all afflicted surfaces.

EXAMPLE 13

The subject presented with superficial bilateral lacerations to the knees. One knee was topically treated with a composition according to Example 3 and the other left untreated as a control. The treated knee healed 50% faster than the control. Erythema and scarring were also much less pronounced on the treated knee.

EXAMPLE 14

The subject suffered from acute post-surgical psoriasis on both elbows and her right knee. Symptoms included scaling, itching and edema. Topical treatment of both elbows with the composition of Example 3 resulted a greater than 70% reduction in the frequency of attacks with a nearly 50% decrease in size of the afflicted surface area and nearly complete absence of scaling. The right knee, as a control, was treated with Diprolene which resulted in no change in frequency of attack and an increase in afflicted surface area.

EXAMPLE 14

The subject had suffered from psoriasis of the elbows for 15 years. Treatment of the elbows with the composition of Example 3 resulted in immediate results and ultimately became symptom free. The subject continues preventative treatment once a week, and at last report remained symptom free.

The foregoing is merely illustrative of the invention and in no way meant to be limiting. Thus, one of skill in the art will immediately recognize other embodiments within the scope of the invention.

What is claimed is:

1. A skin-treating composition consisting essentially of 0.5% to 5% by weight of purcellin oil, and a topically acceptable vehicle.

2. The composition of claim 1, wherein said topically acceptable vehicle comprises about 40% to about 80% Eutanol G.

3. The composition of claim 2, wherein said topically acceptable vehicle further comprises about 20% to about 50% of ethanol.

4. The composition of claim 3 wherein said topically acceptable vehicle comprises about 45% to about 60% Eutanol G, and about 40% to about 50% ethanol, wherein the percentages are all w/w and represent the proportion of one specified ingredient relative to the other two specified ingredients, disregarding the contribution made by any additional ingredients.

5. The composition of claim 4 comprising about 1% purcellin oil, about 52% Eutanol G, and about 47% ethanol.

6. The composition of claim 1 further comprising an aerosol propellant.

7. The composition of claim 6, wherein said propellant is a mixture of equal weights of butane and propane.

8. The composition of claim 1, comprising from about 0.5% to about 1.5% w/w purcellin oil, about 39% w/w Eutanol G, about 35% w/w ethanol, about 12% w/w butane and about 12% w/w propane.

9. The composition of claim 1, comprising one or more additional ingredients selected from the group consisting of age spots removing agents, keratoses removing agents, analgesics, anesthetics, antiacne agents, antibacterial agents, antiyeast agents, antifungal agents, antiviral agents, antiburn agents, antidandruff agents, antidermatitis agents, antipruritic agents antiperspirants, antiinflammatory agents, antihyperkeratolytic agents, antidryskin agents, antipsoriatic agents, antiseborrheic agents, astringents, softeners, emollient agents, coal tar, bath oils, sulfur, rinse conditioners, foot care agents, hair growth agents, powder, shampoos, skin bleaches, skin protectants, soaps, cleansers, antiaging agents, sunscreen agents, wart removers, vitamins, tanning agents, topical antihistamines, hormones, vasodilators and retinoids.

10. The method of claim 9, wherein said inflammatory skin condition is an inflammatory lesion.

11. A method for treating an inflammatory skin condition, comprising topically administering a skin-treating composition, consisting essentially of 0.5% to 5% by weight of purcellin oil in a topically acceptable vehicle, to a patient suffering from an adverse skin condition, wherein the amount of purcellin oil administered to the patient is effective in ameliorating the symptoms of the inflammatory skin condition.

12. The method of claim 11, wherein said inflammatory skin condition is selected from the group consisting of psoriasis, eczema, acne, cold sores, dry skin, sunburn, cuts, insect bites, surgical scars, pruritis and herpesvirus lesions.

13. The method of claim 12, wherein said inflammatory skin condition is psoriasis.

14. The method of claim 12, wherein said inflammatory skin condition is eczema.

15. The method of claim 12, wherein said inflammatory skin condition is sunburn.

16. The method of claim 12, wherein said inflammatory skin condition is acne.

17. The method of claim 12, wherein said inflammatory skin condition is a surgical scar.

18. The method of claim 12, wherein said inflammatory skin condition is a herpesvirus lesion.

* * * * *

UNITED STATES PATENT AND TRADEMARK OFFICE
CERTIFICATE OF CORRECTION

PATENT NO.       : 6,096,326
APPLICATION NO.  : 08/912070
DATED            : August 1, 2000
INVENTOR(S)      : Hugo Allen Wikholm It is certified that error appears in the above-identified patent and that said Letters Patent is hereby corrected as shown below:

Column 8, claim 10, line 20, delete "method" and replace it with -- composition --.

Signed and Sealed this

Twenty-sixth Day of June, 2007

JON W. DUDAS
*Director of the United States Patent and Trademark Office*